United States Patent [19]
Pelerin

[11] Patent Number: 4,619,610
[45] Date of Patent: Oct. 28, 1986

[54] DENTAL IMPRESSION TRAY

[76] Inventor: Joseph J. Pelerin, 2027 Klingensmith, Bloomfield Hills, Mich. 48013

[21] Appl. No.: 754,944

[22] Filed: Jul. 15, 1985

[51] Int. Cl.<sup>4</sup> ............................................... A61C 9/00
[52] U.S. Cl. .................................................... 433/41
[58] Field of Search ................... 433/38, 37, 8, 42, 41

[56] References Cited
U.S. PATENT DOCUMENTS

| | | | |
|---|---|---|---|
| 3,250,004 | 5/1966 | Jones | 433/38 |
| 4,449,927 | 5/1984 | Taylor et al. | 433/38 |

*Primary Examiner*—Robert Peshock
*Attorney, Agent, or Firm*—Gifford, Groh, VanOphem, Sheridan, Sprinkle & Dolgorukov

[57] ABSTRACT

The present invention provides a dental impression tray having a pair of spaced side walls which form a channel therebetween. A layer of wax or thermoplastic material extends between and rigidly secures the sidewalls together and divides the channel into a first and second subchannel. The first subchannel is adapted to receive a setable impression material, such as silicone, for making a dental impression.

16 Claims, 5 Drawing Figures

U.S. Patent   Oct. 28, 1986   4,619,610
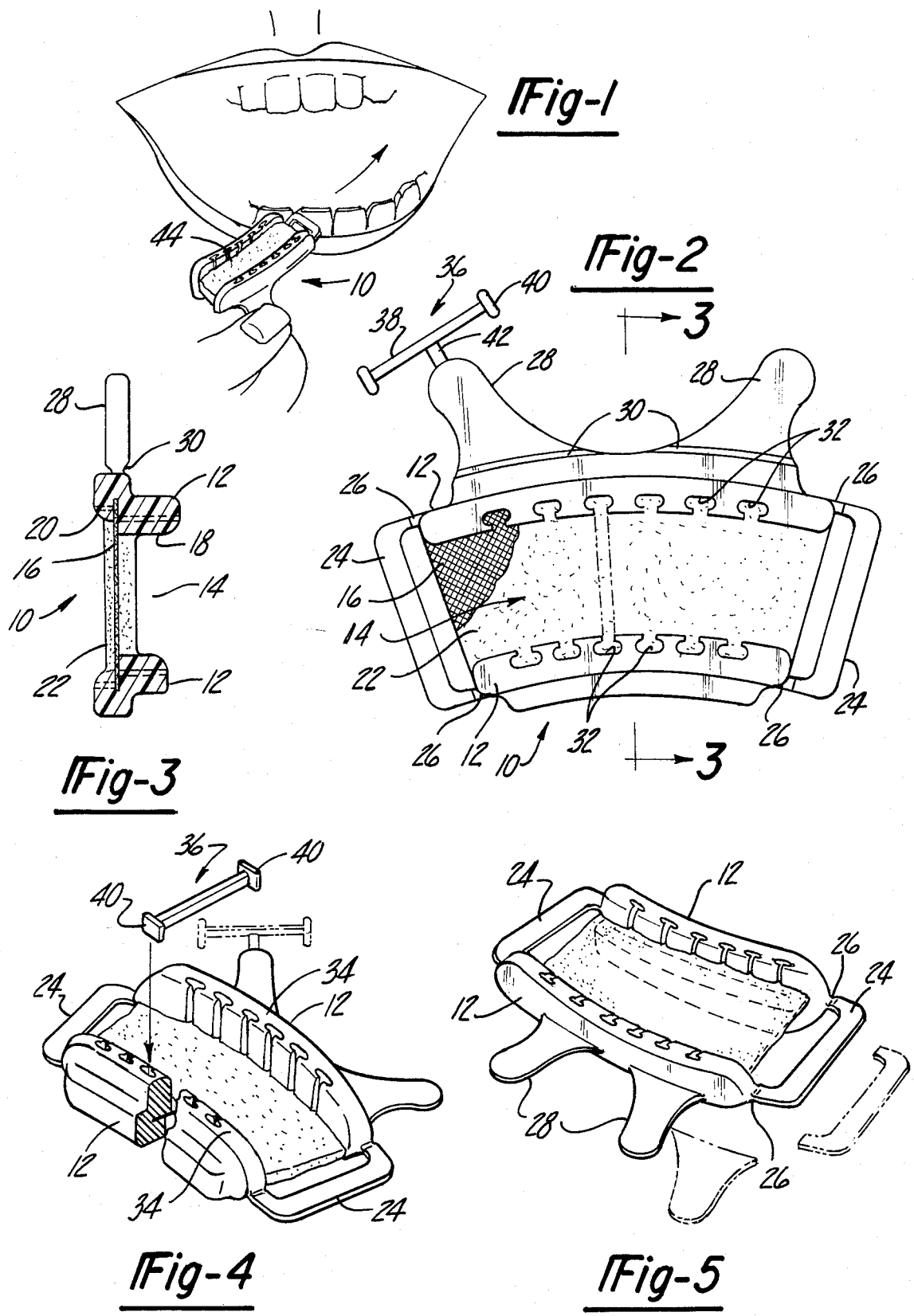

DENTAL IMPRESSION TRAY

BACKGROUND OF THE INVENTION

I. Field of the Invention

The present invention relates to a dental impression tray.

II. Description of the Prior Art

One type of previously known dental impression trays comprises a pair of spaced sidewalls which form a channel therebetween. The side walls are attached together at one end by a cross brace. Furthermore, typically the sidewalls together with the cross brace are of a one piece plastic construction.

A layer of gauze also extends between a midpoint of the sidewalls and thus divides the channel into a first and second subchannel. In use, both subchannels are filled with a settable impression material, such as silicone, and the impression tray is positioned between the upper and lower teeth of the patient. Thus, when the patient bites into the tray channels and retains the bite until the impression material has set, a dental impression of the patient's teeth is made in the impression material.

One disadvantage of these previously known impression trays, however, is that the sidewalls are not rigidly secured to each other and, for that reason, can flex when the dental impression is being made. Such flexing can, for example, be caused by interference between the tray and the patient's gums. Furthermore, upon removal of the tray from the mouth, the sidewalls of the impression tray revert or bend back to their former or unstressed position which results in an inaccurate impression of the patient's teeth. Such inaccuracies in the old create inaccuracies in the bridge, crown or the like which is formed from the mold and requires excessive chair time for the dentist to correct. Furthermore, in some cases, the inaccuracy of the bridge work is so great that new bridge work must be constructed.

A still further disadvantage of these previously known dental impression trays is that such previous impression trays are incapable of measuring the bite tracing of the patient which is representative of the normal range of bite of the patient due to the mobility of the jaw. Without such bite tracing, interference between the patient's upper and lower teeth can occur even when the dental impression is properly made.

A still further disadvantage of these previously known dental impression trays is that, since both sides of the tray are filled with a dental impression material, a relatively large amount of impression material is required for each dental impression. Such impression material is relatively expensive and increases the overall cost of making the dental impression.

A still further disadvantage of these previously known trays is that, due to the relatively flexible construction of the tray, the impression material is oftentimes inadequately forced around the patient's gum when the impression is taken. When this occurs, it is necessary to retake the impression.

SUMMARY OF THE PRESENT INVENTION

The present invention provides a dental impression tray which overcomes all of the above mentioned disadvantages of the previously known devices.

In brief, the impression tray of the present invention comprises a pair of spaced sidewalls which form a channel therebetween. The sidewalls can be dimensioned to either take a quadrant impression or a full arch.

A layer of rigid material, preferably wax or a thermosetting plastic material, extends perpendicularly between a midpoint of the sidewalls. This material layer divides the channel between the sidewalls into a first subchannel and a second subchannel. Preferably the second subchannel is wider than the first.

In use, the first subchannel is filled with a dental impression material and the dental tray is positioned in between the patient's upper and lower teeth so that the first subchannel faces the area of the patient's mouth for which the impression is desired. Furthermore, when the dental impression is being taken, the layer of rigid material once heated in hot water, allows a bite tracing of the patient's teeth opposite the impression area to minimize the possibility of interference between the patient's upper and lower teeth.

The layer of rigid material extending between the sidewalls of the tray minimizes flexing of the tray during use and inaccuracies of the impression caused by such flexing. However, in the preferred embodiment of the invention, a brace extends between the sidewalls at each end in order to further rigidify the tray. Each brace is connected to the sidewalls by frangible portions which enable the dentist to selectively break off the brace from either of the trays. This provision thus allows the dental impression tray to be used in two different quadrants of the mouth. In addition, detachable braces can also be inserted between the sidewalls at a midpoint between their ends to further increase the rigidity of the tray if desired.

BRIEF DESCRIPTION OF THE DRAWING

A better understanding of the present invention will be had upon reference to the following detailed description, when read in conjunction with the accompanying drawing wherein like reference characters refer to like parts throughout the several views, and in which:

FIG. 1 is a perspective view illustrating a preferred embodiment of the present invention;

FIG. 2 is a top view illustrating the preferred embodiment of the present invention;

FIG. 3 is a sectional view taken substantially along line 3—3 in FIG. 2;

FIG. 4 is a fragmentary perspective view illustrating the preferred embodiment of the present invention; and FIG. 5 is a rear perspective view of the preferred embodiments.

DETAILED DESCRIPTION OF A PREFERRED EMBODIMENT OF THE PRESENT INVENTION

With reference first to FIGS. 2 and 3, a preferred embodiment of the dental impression tray 10 of the present invention is thereshown and comprises a pair of sidewalls 12 which are spaced apart and generally parallel to each other and form a channel 14 therebetween. Furthermore, as best shown in FIG. 2, the sidewalls 12 are somewhat arcuate in shape and design to fit within a quadrant of the mouth. It will be understood however, that the sidewalls 12 can have other shapes, for example, a full arch, while remaining within the scope and spirit of the present invention.

Still referring to FIGS. 2 and 3, a layer of gauze 16 extends perpendicularly in between the sidewalls 12 and divides the channel 14 into a first subchannel 18 and a second subchannel 20 (FIG. 3). The second subchannel 20 has a greater width and a smaller depth than the subchannel 18 for a purpose to be subsequently described.

The gauze 16 is impregnated with a rigid material 22 such as wax or a thermosetting plastic, which rigidly secures the sidewalls 12 together. The material 22, however, is sufficiently malleable after heating in hot water (typically 100° F.) to enable a patient to bite into it and to make an impression or indentation in the material 22 when doing so.

With reference particularly to FIGS. 2 and 5, a cross brace 24 extends between and secures the sidewalls 12 together at each end of the sidewalls 12. These cross braces 24 thus further rigidify the sidewalls 12 against flexing when an impression is taken. These braces 24, however, are secured to the sidewalls 12 by a frangible or reduced area portion 26 which allows the braces 24 to be separated from the sidewalls 12 by the dentist as shown in phantom line in FIG. 5. Thus, removal of the brace 24 at one end allows the impression tray to be inserted into one quadrant of the mouth while, conversely, removal of the other brace 24 allows the tray to be inserted into the diametrically opposite quadrant of the mouth.

Still referring to FIGS. 2 and 5, a pair of handles 28 are secured to and extend outwardly from one side of one sidewall 12. These handles are attached to the sidewall 12 by a frangible portion 30 which allows the handles to be selectively removed as shown in phantom line in FIG. 5 by the dentist depending upon in which quadrant the dental tray is positioned.

Preferably, the sidewalls 12, braces 24 and handles 28 are of a one piece plastic construction for low cost manufacture.

With reference now to FIGS. 2 and 4, in some instances additional rigidity between the sidewalls 12 is desirable in order to prevent flexing when taking an impression. Consequently, each sidewall preferably includes a plurality of longitudinally spaced T slots 32 so that the T slots 32 on one side wall 12 face the T slots 32 on the other sidewall 12. Furthermore, each of these T slots 32 are open to a top surface 34 of the sidewalls 12.

A strengthening rib 36 having an elongated shank 38 and a short cross bar 40 at each end is detachably secured to one handle 28 (FIG. 2) by a frangible connection 42. With the rib 36 disconnected from the handle 28 as shown in FIG. 4, the cross bars 40 are slidably received within facing T slots 32 on the sidewalls 12 which further rigidifies and prevents flexing of the sidewalls 12.

In operation, one brace 24 and one handle 28 are removed from the dental tray as shown in phantom line in FIG. 5 and the first subchannel 18 is filled with a settable impression material 44, such as silicone, as shown in FIG. 1. The tray 10 after heating in hot water is then inserted into the patient's mouth between the upper and lower teeth and the patient bites against the tray 10 in his or her normal fashion.

Upon biting against the tray 10, the impression material 44 is forced upwardly around the patient's teeth in the desired fashion while the patient's lower teeth contact the layer of rigid material 22 in the second subchannel 20. Once the silicone material is set and by moving his or her lower jaw slightly, the patient creates a bite trace in the layer of rigid material 22 so that, after the impression material 44 has set, the dentist can check for any possible interference between the lower and upper teeth. Furthermore, either within the patient's mouth or after removing the tray from the patient's mouth, the tray is preferably sprayed with cold water to rigidify the thermoplastic material.

A primary advantage of the present invention is that the sidewalls 12 are rigidly secured together by the layer of material 22 so that flexing of the sidewalls 12 during the impression process is completely avoided. This in turn eliminates the previously known inaccuracies caused by flexing of the tray during the impression process.

A still further advantage of the present invention is that, since only the first subchannel 18 is filled with impression material, the amount of impression material used during the impression process is effectively reduced by one half. Furthermore since the second subchannel 20 is wider and shallower than the first subchannel 18, the possibility of interference between the patient's lower teeth or gums and the tray 10 is eliminated.

Having described my invention, however, many modifications thereto will become apparent to those skilled in the art to which it pertains without deviation from the spirit of the invention as defined by the scope of the appended claims.

I claim:

1. A dental impression tray comprising:
    a pair of spaced sidewalls forming a channel therebetween, and
    means for connecting said sidewalls together comprising a layer of rigid material extending perpendicularly between said sidewalls at a midpoint of said sidewalls, said layer dividing said channel into a first subchannel and a second subchannel, said first subchannel adapted to receive a settable dental impression material
    wherein said layer material is of a composition such that, when heated, said layer material is deformable in a direction perpendicular to the plane of said layer by a human biting into said layer and, when cooled, said layer material retains any deformations caused by a human biting into said layer, whereby a bite trace can be formed on said layer.

2. The invention as defined in claim 1 wherein said second subchannel is wider than said first subchannel.

3. The invention as defined in claim 1 wherein said layer material comprises wax.

4. The invention as defined in claim 1 wherein said connecting means comprises a pair of braces, one brace extending between said sidewalls adjacent each end.

5. The invention as defined in claim 4 wherein said braces are connected to said sidewalls by a frangible portion.

6. The invention as defined in claim 5 wherein each said frangible portion comprises a reduced area portion.

7. The invention as defined in claim 1 and comprising a reinforcing rib and means for attaching said rib between said sidwalls at a midpoint between the ends of said sidewalls.

8. The invention as defined in claim 7 wherein said attaching means comprises a plurality of T slots formed in said sidewalls so that the T slots on one sidewall face the T slots on the other sidewall and wherein said rib comprises an elongated shank having a cross bar at each end which is slidably received in said T slots.

9. The invention as defined in claim 8 wherein said cross bar together with a portion of said shank is substantially identical in shape to said T slots.

10. The invention as defined in claim 1 and comprising a sheet of gauze embedded in said layer.

11. The invention as defined in claim 1 and comprising a handle extending outwardly from one side of one sidewall.

12. The invention as defined in claim 11 and comprising at least two handles extending outwardly from one side of one sidewall, said handles being longitudinally spaced from each other along said one sidewall, and said handles each being secured to said one sidewall by a frangible portion.

13. The invention as defined in claim 1 wherein said layer material comprises a thermosetting material.

14. A dental impression tray comprising:
a pair of spaced sidewalls forming a channel therebetween, and
means for connecting said sidewalls together comprising a layer of rigid material extending perpendicularly between said sidewalls at a midpoint of said sidewalls, said layer dividing said channel into a first subchannel and a second subchannel, said first subchannel adapted to receive a settable dental impression material, and a reinforcing rib and means for attaching said rib between said sidewalls at a midpoint between the ends of said sidewalls wherein said attaching means comprises a plurality of T slots formed in said sidewalls so that the T slots on one sidewall face the T slots on the other sidewall and wherein said rib comprises an elongated shank having a cross bar at each end which is slidably received in said T slots.

15. The invention as defined in claim 14 wherein said cross bar together with a portion of said shank is substantially identical in shape to said T slots.

16. A dental impression tray comprising:
a pair of spaced sidewalls forming a channel therebetween, and
means for connecting said sidewalls together comprising a layer of rigid material extending perpendicularly between said sidewalls at a midpoint of said sidewalls, said layer dividing said channel into a first subchannel and a second subchannel, said first subchannel adapted to receive a settable dental impression material and,
at least two handles extending outwardly from one side of one sidewall, said handles being longitudinally spaced from each other along said one sidewall, and said handles each being secured to said one sidewall by a frangible portion.

* * * * *